US012788707B2

(12) United States Patent
Matelo et al.

(10) Patent No.: US 12,788,707 B2
(45) Date of Patent: Nov. 10, 2026

(54) COMPOSITION FOR THE TREATMENT AND/OR PREVENTION OF THE ORAL DISEASES

(71) Applicant: OBSCHESTVO S OGRANICHENNOI OTVETSTVENNOSTYU "WDS", Moscow (RU)

(72) Inventors: Svetlana Konstantinovna Matelo, Moskovskaya oblast (RU); Aleksandr Vladimirovich Grosser, Moskovskaya oblast (RU); Tatiana Vladimirovna Kupets, Moskovskaya oblast (RU)

(73) Assignee: OBSCHESTVO S ORGANICHENNOI OTVETSTVENNOSTYU "WDS", Moscow (RU)

( * ) Notice: Subject to any disclaimer, the term of this patent is extended or adjusted under 35 U.S.C. 154(b) by 571 days.

(21) Appl. No.: 18/023,264

(22) PCT Filed: Aug. 23, 2021

(86) PCT No.: PCT/RU2021/050275
§ 371 (c)(1),
(2) Date: Feb. 24, 2023

(87) PCT Pub. No.: WO2022/045933
PCT Pub. Date: Mar. 3, 2022

(65) Prior Publication Data

US 2023/0320976 A1 Oct. 12, 2023

(30) Foreign Application Priority Data

Aug. 24, 2020 (RU) ................................ 2020128107

(51) Int. Cl.
*A61K 8/9789* (2017.01)
*A61Q 11/00* (2006.01)

(52) U.S. Cl.
CPC ............ *A61K 8/9789* (2017.08); *A61Q 11/00* (2013.01)

(58) Field of Classification Search
CPC ......... A61K 8/9789; A61K 36/76; A61P 1/00; A61P 1/02; A61P 17/02; A61Q 11/00;
(Continued)

(56) References Cited

U.S. PATENT DOCUMENTS

2011/0117033 A1* 5/2011 Manasherov ............. A61P 1/02 424/57
2014/0242198 A1* 8/2014 Modak .................. A61K 36/31 424/770
(Continued)

FOREIGN PATENT DOCUMENTS

AE 200801824 A1 8/2009
KR 10-2086766 3/2020
(Continued)

OTHER PUBLICATIONS

Espacenet Translation of RU2416391C1 (Year: 2011).*
(Continued)

*Primary Examiner* — Sahana S Kaup
*Assistant Examiner* — Amanda Michelle Petritsch
(74) *Attorney, Agent, or Firm* — MCANDREWS HELD & MALLOY, LTD.

(57) ABSTRACT

The group of inventions relates to healthcare, concerns dentistry. The group of inventions includes a composition for the treatment and/or prevention of the oral diseases comprising an effective amount of aqueous and lipophilic extracts of aspen bark and at least one or more auxiliary compounds for the treatment and/or prevention, also
(Continued)

includes a method of treatment and the use of a composition for the manufacture of a product for the treatment and/or prevention of the oral diseases. The group of inventions is characterized by high efficiency in the treatment and/or prevention of various the oral diseases, provides high-quality hygienic cleaning of the surface of the teeth and oral cavity. The use of a group of inventions makes it possible to reduce the likelihood of the occurrence and/or elimination of inflammation, as well as ulcers and erosions of the oral cavity in situations that contribute to their formation.

14 Claims, 1 Drawing Sheet

(58) Field of Classification Search
CPC .. B01D 11/02; B01D 11/0203; B01D 11/0288
See application file for complete search history.

(56) References Cited

U.S. PATENT DOCUMENTS

| | | | |
|---|---|---|---|
| 2023/0053438 | A1 | 2/2023 | Hall |
| 2023/0053827 | A1 | 2/2023 | Nguyen |
| 2023/0054010 | A1 | 2/2023 | Oltmanns |
| 2023/0058941 | A1 | 2/2023 | Carlson |

FOREIGN PATENT DOCUMENTS

| | | | |
|---|---|---|---|
| RU | 2090183 | C1 | 9/1997 |
| RU | 2263499 | | 10/2005 |
| RU | 2416391 | C1 | 4/2011 |
| SU | 1814553 | | 5/1993 |
| UA | 73209 | | 6/2005 |

OTHER PUBLICATIONS

Annabelle St-Pierre et al., "Phytochemical Screening Of Quaking Apsen (*Populus tremuloides*) Extracts by UPLC-QTOF-MS and Evaluation of their Antimicrobial Activity", Molecules, 2018, vol. 23, published Jul. 16, 2018, Basel, Switzerland.

B.N. Kuznetsov et al., "Isolation and Study of Extractive Bark Products Aspen", Chemistry of plant materials, 1998, No. 3, pp. 5-12, Institute of Chemistry and Chemical Technology SB RAS, Krasnoyarsk, Russia.

PCT International and Search Report and Written Opinion for PCT Patent Application No. PCT/RU2021/050275 mailed Dec. 2, 2021.

Unknown, "R.O.C.S. Junior Natural toothpaste for children 6-12 years old—effective and pleasant prevention of dental Diseases", Feb. 5, 2019, Unident.

S.I. Borodovitsina et al. "Dental disease prevention", Learning guide, 2019, Ryazan, p. 55 (Machine Translation and Russian Submitted).

* cited by examiner

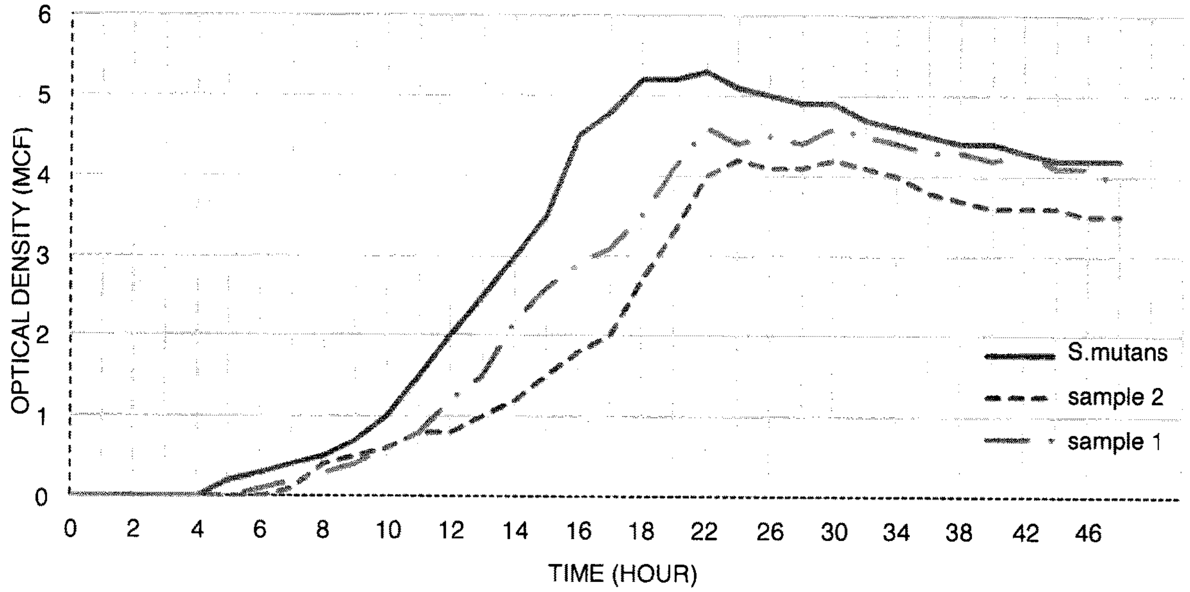
6
5
4
3
2
1
0
OPTICAL DENSITY (MCF)
0 2 4 6 8 10 12 14 16 18 22 26 30 34 38 42 46
TIME (HOUR)
S.mutans
sample 2
sample 1

COMPOSITION FOR THE TREATMENT AND/OR PREVENTION OF THE ORAL DISEASES

CROSS-REFERENCE TO RELATED APPLICATIONS

This application is a national stage entry of International Patent Application No. WO 2022/045933 A1, filed on Aug. 23, 2021, titled "Composition for the treatment and/or prevention of the oral diseases," which claims priority from Russian Patent Application No. 2020128107, filed on Aug. 24, 2020, titled "Composition for the treatment and/or prevention of the oral diseases," the disclosures of which are incorporated herein by reference in their entirety.

BACKGROUND

The present group of inventions relates to healthcare, more specifically concerns dentistry and is intended for the treatment and/or prevention of the oral diseases. The group of inventions includes a composition for the treatment and/or prevention of the oral diseases comprising an effective amount of aqueous and lipophilic extracts of aspen bark and at least one or more auxiliary compounds for the treatment and/or prevention. The group of inventions also includes the use of a composition for the manufacture of a product for the treatment and/or prevention of the oral diseases.

According to the World Health Organization the oral diseases are among the most common non-communicable diseases and affect people throughout their lives, causing pain and discomfort, leading to tooth loss and the occurrence of concomitant diseases.

This not only reduces the quality of life, leads to aesthetic the oral diseases, but in some cases, the oral diseases (with complications) can cause permanent incapacitation, lead to disability. Today, about half of the world's population suffers from the oral diseases, the most common of which are dental caries, periodontal diseases, diseases caused by injuries of the oral cavity, etc.

Treatment of such diseases is expensive and time-consuming. In most high-income countries, dentistry accounts for, on average, 5% of all health care costs and about 20% of health care costs from own funds.

The high cost and painful treatment process lead to irregularity and untimely treatment to the dentist, thereby causing the development of complications, tooth loss, the occurrence of serious diseases such as acute and chronic forms of stomatitis, periodontal diseases, for example, gingivitis, periodontitis or parodontosis, dental caries, pulpitis, increases the likelihood of inflammation, as well as ulcers and erosions of the oral cavity in situations that contribute to their formation.

The solution to the above problems is timely and appropriate prevention, as well as effective complex therapy aimed at obtaining an effect throughout the oral cavity.

Today, a large number of dental care products of various shapes and compositions are available for sale, designed for their regular use.

The most common of them are toothpastes, mouthwashes, gum balms, non-abrasive gels for teeth and/or gums.

However, most of them have only a cleansing and cosmetic effect.

Products comprising active substances in their composition, in particular, anti-carious and/or inflammatory agents, as a rule, are characterized by a narrowly directed action and a short duration of action after use, which generally indicates their low therapeutic effectiveness. Preventive and therapeutic products for home use do not provide sufficiently effective prevention.

The purpose of the present invention is to create a composition that is effective in the treatment and/or prevention of various the oral diseases, having a complex effect and a long-lasting effect even at home.

To achieve this goal, the authors have created a composition of preventive and/or therapeutic action comprising an effective amount of aqueous and lipophilic extracts of aspen bark for treatment and/or prevention, and at least one or more acceptable carriers and/or auxiliary agents.

It was found that the simultaneous inclusion of aqueous and lipophilic extracts of aspen bark in a composition characterized by one or more auxiliary agents and/or carriers disclosed in the description makes it possible to create an effective complex therapeutic and/or preventive long-acting product suitable for home use. Taking into account the conducted experiments, it can be argued that the use of aqueous and lipophilic extracts of aspen bark in the composition gives an effect significantly greater than the use of these extracts in the composition separately.

Dental compositions comprising a separate aqueous extract of aspen bark are known from the prior art.

For example, from the patent of the RU 2263499, a dental elixir is known comprising ethyl alcohol, polyatomic alcohol, extracts of vegetable raw materials, essential oils, a flavor additive and drinking water, wherein it additionally comprises lignans from lignan-containing plants, selenocysteine, as extracts of vegetable raw materials—water extracts of bog strawberry, stevia leaves, turnip leaves, cerapadus leaves, aspen bark, as essential oils—oils tea tree and myrrh, and as a flavoring additive—rebaudioside A.

The authors of RU 2263499 patent indicate that the addition of aspen bark extract to the proposed composition is aimed at increasing the remineralizing properties of the elixir. However, the authors do not investigate the remineralizing properties of the composition and do not disclose the necessary amounts to achieve a remineralizing effect.

From the author's certificate SU 1814553, a composition for the prevention of periodontal diseases is known, comprising a plant extract, ethyl alcohol, menthol, flavoring agent and water, characterized in that, in order to increase activity by improving the permeability of the oral mucosa, it additionally comprises polyvinylpyrrolidone, sodium lauryl sulfate, an antiseptic, and as a plant extract—an aqueous extract of aspen bark with the following component content, wt. %: an aqueous extract of aspen bark 20.0-25.0; polyvinylpyrrolidone 4.0-6.0; sodium lauryl sulfate 1.0-3.0; antiseptic preservative (propyl ether of paraoxybenzoic acid or sodium benzoate) 0.2-0.5; ethyl alcohol (96°) 10.0-20.0; menthol 1.0-1.8; flavoring agent 0.7-1.5; water up to 100.

The description of the document states that the water extract of aspen bark comprises glycosides (salicin, salicortin, etc.), up to 10% of tannins, essential oils, phytoncites, amino acids, macro- and microelements, substances with P-vitamin activity (coumarins and flavonoids) and other biologically active substances. They have anti-inflammatory, anti-radiation, antiseptic and hemostatic, as well as astringent effect. Due to the latter, the permeability of the oral mucosa to biologically active substances increases, which improves the trophism of periodontal tissues, has a therapeutic and preventive and healing effect.

Therapeutic and prophylactic toothpaste "Osinka", known from the patent of the RU 2090183, comprises plant extracts, chalk, glycerin, sodium carboxymethylcellulose, flavoring agent, aerosil, sodium lauryl sulfate, perfume oil, antiseptic preservative and water, gliderinine sodium salt, polyvinylpyrrolidone, xylitol-sorbitol syrup and an aqueous extract of aspen bark.

The authors point out that the introduction of an aqueous extract of aspen bark into the paste, comprising glycosides, tannins, essential oils, phytoncides and other biologically active components, and licorice preparations provides its hemostatic, healing, anti-radiation, antiseptic, astringent effect.

The products disclosed above comprise only an aqueous extract of aspen bark as an active agent.

However, in addition to water-soluble components, aspen bark comprise substances that are soluble in organic solvents. When extracting aspen bark with water, as a rule, tannins, organic acids, mineral salts, etc. are released.

Extraction with organic solvents allows to isolate fats, resins, waxes, essential oils, vitamins that are not available during water extraction, as well as phenol glycosides and flavonoids.

The extract of diethyl ether of the aspen bark crust is active against such bacterial species as *Bacillus subtilus, Escherichia coli; Clavibacter* m.s. *michiganensis, Xanthomonas compestris*, etc. (Natalia Mikhailovna Faustova, dissertation submitted in partial fulfillment of the requirements for the degree of candidate of chemical sciences, Chemical composition of aspen bark and wood, St. Petersburg 2005, p. 7). The fractions of phenol glycosides and flavonoids isolated from the ethanol extract exhibit anti-ulcer activity: they reduce the prevalence of the ulcerative process by 40% and 50%, respectively. As the active principle of such medicines, dry aspen bark extract obtained by extracting raw materials with 40% ethanol is used (Chalmers, R. A. A Method for the Determination of Phosphorus in organic compounds./R. A Chalmers, D. A Thompson. Anal. Chim. Acta. 1958. Vol. 18, N4-6.-P. 575-577).

The composition according to the present invention uses an aqueous extract and a lipophilic one prepared by extraction of aspen bark with liquefied carbon dioxide, which allows the most complete use of the components of aspen bark that are useful in the prevention of the oral diseases.

The resulting composition is characterized by high efficiency in the treatment and/or prevention of various the oral diseases compared to compositions that include only an aqueous extract of aspen bark, action against various pathogens of the oral diseases and a long-lasting effect.

The use of such a composition reduces the likelihood of the occurrence and/or elimination of inflammation, as well as ulcers and erosions of the oral cavity in situations that contribute to their formation.

Such situations include the action of the causative agent of a bacterial infection, chemical or thermal burn of the oral cavity, injury of the oral cavity with a sharp object, etc.

The present invention also concerns the use of the described composition for the treatment and/or prevention of the oral diseases. Moreover, when using this composition simultaneously with the effect of treatment and/or prevention, a high quality of hygienic cleaning of the surface of the teeth and the oral cavity as a whole is ensured.

The use of the claimed composition allows to increase the buffer capacity of saliva, normalize its pH and increase its mineralizing potential. These properties allow the composition to be used in patients with non-removable orthodontic equipment who are on long-term orthodontic treatment.

The effects presented above can be regarded as a technical result of a group of inventions.

Conditions and/or diseases for which the proposed compositions have a preventive effect, without limitation, include acute and chronic forms of stomatitis, periodontal diseases, for example, gingivitis, periodontitis or parodontosis, dental caries, pulpitis.

The compositions of the invention also prevent the formation of plaque and/or dental calculus.

The compositions of the invention also contribute to the healing of injuries of the oral cavity and teeth.

EMBODIMENT OF THE INVENTION

Alcohol extraction does not provide the lipophilic extract used in this composition, since it has a significant drawback: before alcohol extraction, the lipid complex is not extracted, which creates certain difficulties in isolating the target products and requires the introduction of a purification stage (Natalia Mikhailovna Faustova, dissertation submitted in partial fulfillment of the requirements for the degree of candidate of chemical sciences, Chemical composition of aspen bark and wood, St. Petersburg 2005).

For the preparation of a lipophilic extract according to the present invention, liquefied carbon dioxide is used.

Liquefied carbon dioxide is a colorless, easily mobile liquid, the viscosity is 14 times less than the viscosity of water, 5 times less than ethyl alcohol. Such properties of carbon dioxide distinguish it as an extractant with the best diffusion properties. The boiling point of liquefied CO2, depending on the saturated vapor pressure, ranges from −56.6 to +31° C., which creates a wide range of regulation of low-temperature distillation of $CO_2$ from extracts with almost no residue. This property allows you to remove the extractant from the extracts quickly even with a slight temperature effect and keep the extracted substances in the native state. Low values of the heat of vaporization (condensation) indicate a relatively small energy consumption required for evaporation and condensation of the solvent when using it in the technological cycle.

Liquefied $CO_2$ is a strong and inert substance that exhibits complete chemical indifference to processed raw materials, recoverable substances, and structural materials of equipment. The dielectric constant for liquefied $CO_2$ at 10° C. is 2.6. This value of the dielectric constant is characteristic of nonpolar solvents, which makes it possible to extract nonpolar or weakly polar substances from the crust. These include essential and fatty oils; carbonyl compounds; fat-soluble vitamins (A, D, K, F, E); sterols; alkaloids in the form of bases, etc.

Extraction and distillation of the solvent at a low temperature (up to 30° C.) makes it possible to extract essential oils and biologically active components in the native state. Liquid $CO_2$ does not support the vital activity of microorganisms and mold fungi, which makes it possible to obtain sterile extracts. Extraction in a liquid $CO_2$ environment completely eliminates oxidation due to the absence of aeration.

The physico-chemical features of the solvent used contribute to the extraction of substances from plant raw materials practically without changing their properties. Distillation is provided by a pressure reduction that turns liquid $CO_2$ into a gaseous state, while a $CO_2$ extract (lipophilic extract) is released.

The water extract is obtained using standard methods. Extraction can be carried out at room or elevated temperature, extraction can also be carried out using boiling water or aqueous solutions and standard containers and connecting equipment. If necessary, water or an aqueous solution of alkali or an aqueous solution of acid can be used as an extractant, the pH of the solution can be adjusted if necessary, the values and methods are standard and known to specialists in this field.

Extracts according to the invention can be obtained by using suitable techniques, including those known to specialists in this field.

If necessary, extracts can be separated from negative compounds by filtration, chromatography, extraction or other standard techniques.

The quantitative ratio of the aqueous and lipophilic extract of aspen bark in the mixture is 1:1-100:1. The quantitative ratio can be represented by the ratios 1:1, 2:1, 5:1, 10:1, 20:1, 30:1, 40:1, 50:1, 60:1, 70:1, 80:1, 90:1, 100:1, as well as ratios close to this (within the error of the corresponding measurements).

The extracts can be pre-mixed or added to the composition separately.

The proposed composition is used for the manufacture of cosmetic, preventive and/or therapeutic product.

The product can be made in the form of a toothpaste, a non-abrasive gel or a mouthwash.

For the preparation of compositions according to the invention, auxiliary agents such as thickeners, binding agents, abrasive agents (for toothpaste), wetting agents, foaming agents, flavorings, sweeteners, stabilizers, preservatives, anti-caries additives can be used.

An auxiliary substance or auxiliary agent is a substance that contributes to giving the composition an acceptable form and properties for cosmetic, preventive and/or therapeutic use.

Thickeners can be various cellulose derivatives, for example, carboxymethylcellulose, hydroxypropylcellulose, hydroxymethylcellulose, hydroxypropylmethylcellulose, alginates, for example, sodium alginate, carrageenan, xanthan gum, guar gum.

The composition in the form of a toothpaste according to the invention can be prepared using abrasive agents, for example, the following: hydroxyapatites, calcium phosphates, calcium, magnesium, aluminum silicates, silicon oxides, calcium, magnesium carbonates, sodium bicarbonate (baking soda).

The wetting agents in the composition can be glycerin, sorbitol, xylitol, polyethylene glycol or mixtures thereof.

Alkylamidobetaines, laurylsarcosinate salts, methyl cocoyltaurate salts, non-ionic surfactants, for example, PEG-40 hydrogenated castor oil or Polysorbate-20 can be used as surfactants in the composition.

The following flavors can be used in the composition: essential oils or extracts of mint, lemon balm, clove, eucalyptus, orange, lemon, sage, lavender, sandalwood, cypress, etc.

Acceptable sweeteners in the composition of the proposed compositions are, without limitation, saccharin or its derivatives, aspartame or its derivatives, stevioside, neohesperidin dihydrochalcone, glycyrrhizinates, acesulfame potassium, perillartine, p-methoxycoric aldehyde, xylitol.

Vitamins E, C or their derivatives can be used as stabilizers in the composition.

Hydroxybenzoic acid esters, alkyldiaminoethylglycine hydrochloride, parabens, for example, methylparaben, ethylparaben, propylparaben, sodium benzoate, potassium sorbate, ortho-5-cumen-ol can be used as preservatives in the composition.

Calcium glycerophosphate, magnesium glycerophosphate, sodium fluoride, potassium fluoride, sodium monofluorophosphate, potassium monofluorophosphate can be used as anti-caries additives in the composition.

Auxiliary components and/or carriers may be present in the composition from about 0.1% to about 99% wt., in some cases—from about 0.1% to about 1% wt., in some cases—from about 1% to about 10% wt. in some cases—from about 10% to about 99% wt.

The recommended doses of active components for adults are 0.02-3%. For adolescents (up to 25 years), the recommended dose of the extract is up to 65% of the adult dose, for infants and young children—up to 10%, for children from 7 to 14 years—50%.

BRIEF DESCRIPTION OF THE DRAWINGS

FIG. 1. shows the cultivation of *S. mutans* with the studied samples of toothpastes.

EXAMPLES

Example 1. Preparation of Toothpaste

Compositions in the form of toothpaste are prepared as follows.

The required amount of water is weighed in a measuring dispenser, then the water is loaded into a mixer, if necessary, heated to a temperature of 50-60° C. Thickener, wetting agents, sweetener, preservatives, anti-caries additives are added to the water. The mixture is mixed until a homogeneous gel is obtained, if necessary, homogenized and vacuumed. An abrasive filler is added to the resulting gel, mixed until a homogeneous mass is obtained, if necessary, homogenized and vacuumed. If necessary, the resulting mass is cooled to a temperature of 30-40° C., and surfactants, an aqueous extract of aspen bark, stabilizers, and a mixture of fragrance with $CO_2$ extract of aspen bark are added. Mix, homogenize and vacuum if necessary. The manufactured toothpaste is pumped into storage tanks and packed into tubes on filling machines.

Example 2. Preparation of Non-Abrasive Gel

Compositions in the form of a non-abrasive gel are prepared as follows.

The required amount of water is weighed in a measuring dispenser, then the water is loaded into a mixer, if necessary, heated to a temperature of 50-60° C. Thickener, wetting agents, sweetener, preservatives, anti-caries additives are added to the water. The mixture is mixed until a homogeneous gel is obtained, if necessary, homogenized and vacuumed. If necessary, the resulting mass is cooled to a temperature of 30-40° C., and surfactants, an aqueous extract of aspen bark, stabilizers, and a mixture of fragrance with $CO_2$ extract of aspen bark are added. Mix, homogenize and vacuum if necessary. The manufactured gel is pumped into storage tanks and packed into tubes on filling machines.

The compositions according to the invention can be prepared using standard techniques.

Example 3. Examples of Compositions According to the Invention

Below are examples of specific formulations of compositions according to the present invention. These examples are illustrative in nature and are not restrictive. It is clear to the specialist that compositions with the properties of the invention can be implemented in other formulations that meet the characteristics of the invention.

1. Non-Abrasive Gel:

| Component | Example 1, wt. % | Example 2, wt. % |
|---|---|---|
| Glycerin | 15 | 30 |
| Xylitol | 25 | 5 |
| Calcium glycerophosphate | 0.1 | 2 |
| Hydroxyethylcellulose | 1.5 | 3 |
| Water extract of aspen bark | 1 | 5 |
| $CO_2$ extract of aspen bark | 0.5 | 0.05 |
| Polysorbate-20 | 2 | — |
| PEG-40 hydrogenated castor oil | — | 0.6 |
| Methylparaben | 0.3 | 0.1 |
| O-cumene-5-ol | 0.02 | 0.1 |
| Flavoring agent | 0.6 | 0.05 |
| Water | Up to 100 | Up to 100 |

2. Toothpaste:

| Component | Example 3, wt. % | Example 4, wt. % |
|---|---|---|
| Sorbitol | 40 | 20 |
| Xylitol | 8 | 15 |
| Silicon dioxide (abrasive) | 5 | 15 |
| Sodium Fluoride | 0.3 | 0.1 |
| Xanthan gum | 0.8 | 1.2 |
| Water extract of aspen bark | 2 | 3 |
| $CO_2$ extract of aspen bark | 0.2 | 0.1 |
| Alkylamidobetaine | 0.6 | 0.8 |
| Sodium lauroylsarcosinate | 0.5 | 0.2 |
| Sodium Benzoate | 0.8 | 0.5 |
| Potassium Sorbate | 0.2 | 0.4 |
| Sodium saccharin | 0.05 | 0.2 |
| O-cumene-5-ol | 0.05 | 0.08 |
| Flavoring agent | 0.6 | 1.2 |
| Water | Up to 100 | Up to 100 |

The water extract of aspen used in the preparation of compositions is characterized by a mass fraction of water and volatile substances—86.6%; a mass fraction of tannins—2.0%.

Lipophilic (fat-soluble) $CO_2$ extract comprises 4.35% water and volatile substances, 4.0% tannins.

The mixture of extracts is characterized by the presence in its formulation of phenolic glycosides (salicin, salicortin, tremuloicin), tannins, organic acids (oleic, linoleic, palmitic, capric, lauric, arachin, begenic), triterpenoids, pectin, glycine betaine, flavonoids, wax, sterols, carotenoids, polysaccharides, anthocyanins, glycolipids, phospholipids.

Example 4. Antibacterial Activity of the Compositions

A comparative analysis of the antibacterial (*Streptococcus mutans*) action of toothpastes 1 and 2 was carried out using an automated system for monitoring the growth of microorganisms.

In the experimental part, a bioreactor "RTS-1" (BioSan, Latvia) was used, with a mixing system—"reverse-spinner". The system is designed for cultivating microorganisms and evaluating their growth in real time. The results were interpreted by measuring the optical density (OD) at a wavelength of $\lambda$=850 nm.

For the cultivation of *S. mutans*, a liquid nutrient medium—Todd Hewitt Broth (M313)—was used. For the cultivation of microorganisms in the bioreactor, 50 ml tubes with a membrane filter (TubeSpin SW) were used.

Test Samples:

Control sample—suspension of *S. mutans;*

Sample of toothpaste 1;

Sample of toothpaste 2.

TABLE 1

Experimental samples of toothpastes.

| Component | Sample 1, wt. % | Sample 2, wt. % |
|---|---|---|
| Sorbitol | 15 | 15 |
| Glycerin | 15 | 15 |
| Xylitol | 8 | 8 |
| Silicon dioxide | 15 | 15 |
| Xanthan gum | 1.1 | 1.1 |
| Water extract of aspen bark | 1 | 1 |
| $CO_2$ extract of aspen bark | — | 0.3 |
| Alkylamidobetaine | 0.8 | 0.8 |
| Sodium lauroylsarcosinate | 0.4 | 0.4 |
| Sodium Benzoate | 0.4 | 0.4 |
| Sodium saccharin | 0.3 | 0.3 |
| Sodium Fluoride | 0.2 | 0.2 |
| Ortho-cumene-5-ol | 0.05 | 0.05 |
| Flavoring agent | 0.8 | 0.8 |
| Water | Up to 100 | Up to 100 |

For each experiment, a bacterial suspension in the amount of 5 ml was prepared separately in sterile test tubes with a volume of 15 ml. The optical density of the resulting suspension was measured using a DEB-1B densitometer (BioSan, Latvia). The concentration of the test sample was 0.1 g/1 ml.

When cultivating a clinical *S. mutans* isolate, in a control sample, the adaptive phase lasted up to 8 hours. This phase corresponds to the period of physiological adaptation, including the induction of enzymes, synthesis and assembly of ribosomes. The initial stationary period lasted up to 4 hours, 4-6 hours—the period of initial cell growth, 6-8 hours—the period of accelerated development. The exponential phase was marked by a classical jump in the optical density at the interval of 8-16 hours, after which a period of growth delay with a sharp transition to stationary equilibrium is traced. The peak optical density index at the end of true logarithmic development (indicator $\alpha$) is 4.51±0.3 mcf (16 hours), the total indicator for the entire period of culture development (indicator (3) is 5.25±0.3 mcf (16 hours). The stationary phase, characterized by the equilibrium between cell growth and division and the process of cell death, was short (18-24 hours), followed by a gradual transition of the culture into the dying phase. The average optical density in stationary equilibrium is 5.28±0.3 mcf.

Cultivation of the bacterial population of *S. mutans* with the addition of the studied samples of pastes 1 and 2 (refer to FIG. 1) showed the following:

Sample 2—the adaptive phase is significantly prolonged compared to the control sample: up to 6 hours—the initial stationary period; up to 8 hours—the period of initial cell growth; up to 14 hours—the period of accelerated cell development. The period of accelerated cell development is characterized by the beginning of cell division, an increase in the total mass of the population and a constant increase in the growth rate of the culture, but exponential signs of growth were noted only after 15 hours of the experiment. The duration of logarithmic cell development was shortened compared to the control sample, and the rate of generation of new populations, therefore, the change in the optical density index was an order of magnitude lower. The indicator $\alpha$ is 4.15±0.3 mcf (22 hours), the indicator $\beta$ is 4.25±0.3 mcf (24 hours). The stationary equilibrium phase was longer than in the control sample, with an average optical density of 4.25±0.3 mcf (24 hours).

Sample 1—according to the results of cultivation of the bacterial population with this sample, the adaptive phase lasted up to 10 hours. The transition of culture into exponential development was almost instantaneous, without a pronounced acceleration of growth. The indicator α is 4.54±0.3 mcf (20 hours), the indicator β is 4.25±0.3 mcf (22 hours). There is a stationary equilibrium phase with an average optical density of 4.55±0.3 mcf (22-32 h).

TABLE 2

Indicators of key points of the curve

| Sample | Indicator α (mcf) | Indicator β (mcf) | The average indicator in the stationary phase (mcf) | Reduction, % |
|---|---|---|---|---|
| Control | 4.51 ± 0.3 | 5.25 ± 0.3 | 5.28 ± 0.3 | — |
| Toothpaste 1 | 4.54 ± 0.3 | 4.65 ± 0.3 | 4.55 ± 0.3 | 13 |
| Toothpaste 2 | 4.15 ± 0.3 | 4.25 ± 0.3 | 4.25 ± 0.3 | 19 |

Thus, the study of samples of toothpastes 1 and 2 with aspen bark extracts with an automated assessment of the growth curves of the microbial population of *S. mutans* showed the presence of antibacterial activity (bacteriostatic), and sample 2 (comprising an additional 0.3% $CO_2$ of aspen bark extract) showed the best dynamics of this activity with the leading cariesogenic species for the child's body—*S. mutans.*

Example 5. The Effectiveness of Toothpaste in Patients Undergoing Orthodontic Treatment Patients undergoing long-term orthodontic treatment were selected as a model for studying the effectiveness of toothpastes as a special case of the claimed composition.

This group of patients, due to the accelerated formation of plaque and its altered distribution architectonics in the oral cavity, is characterized by an increased intensity of the carious process and a pronounced severity of symptoms of periodontal diseases (severe forms of gingivitis).

65 patients aged 13-15 years were examined. All the subjects were trained in the rules of oral hygiene, all were carried out professional hygiene. Subsequent hygiene was carried out by the subjects independently using orthodontic toothbrushes and brushes. Teeth brushing was carried out three times a day.

The subjects were divided into 3 groups:

The first group carried out oral hygiene using a toothpaste comprising an aqueous and lipophilic extract of aspen bark, (the composition of the paste corresponds to sample 4, disclosed in Example 3);

The second group carried out oral hygiene using a toothpaste comprising only an aqueous extract of aspen bark, (the composition of the paste corresponds to sample 1, disclosed in Example 4);

The third group (control) carried out oral hygiene using a toothpaste that does not comprise aspen extracts, attention was not focused on the specific composition of the paste.

At the first examination of patients, the hygiene efficiency index (O'Leary), the index of the state of periodontal tissues (PMA) was determined, which allows assessing the severity of gingivitis, the rate of salivation, the viscosity of saliva, the buffer capacity of oral fluid.

It was found that all patients who are being treated with non-removable orthodontic equipment have unsatisfactory indicators of oral hygiene. On average, the hygiene index for the three groups was 87.96±1.33%. The saliva viscosity in all patients is lower than the age norm, the buffer capacity is shifted to the acidic region, the salivation rate is lower than the reference values.

These indicators were determined in patients after three months.

Below are the data on the results of the study for each group.

TABLE 3

Results of the study of patients of the first group

| Index | Before the start of the study | After 3 months | Degree of reduction, % |
|---|---|---|---|
| O'Leary, % | 89.56 ± 3.67 | 38.23 ± 3.81 | 57.31 |
| PMA, % | 78.45 ± 3.07 | 29.32 ± 3.12 | 62.63 |
| Salivation rate, ml/min | 0.28 ± 0.03 | 0.29 ± 0.05 | — |
| Saliva viscosity, cPs | 1.98 ± 0.08 | 1.32 ± 0.05 | — |
| Buffering capacity of oral fluid | 6.45 ± 0.03 | 7.10 ± 0.04 | — |

TABLE 4

Results of the study of patients of the second group

| Index | Before the start of the study | After 3 months | Degree of reduction, % |
|---|---|---|---|
| O'Leary, % | 86.78 ± 3.18 | 42.64 ± 4.10 | 50.86 |
| PMA, % | 74.32 ± 3.20 | 38.65 ± 3.65 | 47.99 |
| Salivation rate, ml/min | 0.28 ± 0.03 | 0.29 ± 0.03 | — |
| Saliva viscosity, cPs | 1.98 ± 0.08 | 1.40 ± 0.05 | — |
| Buffering capacity of oral fluid | 6.40 ± 0.03 | 7.05 ± 0.04 | — |

TABLE 5

Results of the study of patients of the third group

| Index | Before the start of the study | After 3 months | Degree of reduction, % |
|---|---|---|---|
| O'Leary, % | 88.18 ± 3.53 | 61.65 ± 3.24 | 30.10 |
| PMA, % | 70.25 ± 3.27 | 67.33 ± 4.76 | 4.16 |
| Salivation rate, ml/min | 0.28 ± 0.03 | 0.29 ± 0.03 | — |
| Saliva viscosity, cPs | 1.98 ± 0.08 | 1.89 ± 0.05 | — |
| Buffering capacity of oral fluid | 6.45 ± 0.03 | 6.53 ± 0.03 | — |

The conducted studies have shown the following. During the study period, there was no significant change in the rate of salivation for patients of all groups. In the subjects of the first and second groups, the hygiene index significantly decreased, which corresponds to a decrease in the amount of plaque and dental calculus. A slight decrease in the O'Leary index is also observed in patients of the control group. The subjects of the first and second groups also have a significant improvement in the condition of the gums at the teeth. In patients of the first and second groups, a decrease in the viscosity of saliva was also observed, which leads to a more complete cleaning of the surfaces of the teeth and oral cavity, and contributes to an increase in its remineralizing potential. The use of a paste comprising extracts of aspen bark leads to a shift in the pH of saliva to a more neutral area.

At the same time, based on the data in tables 3 and 4, it can be seen that the composition, characterized by the presence of two aspen extracts: lipophilic and aqueous, demonstrates excellent properties not only in comparison with the control compositions, but also in comparison with a paste comprising only an aqueous extract of aspen bark.

In general, a method for the prevention and treatment of oral diseases using the composition of the present invention consists in applying it to the surface of the teeth and finding the composition in the oral cavity and on the surface of the teeth for 5 seconds to 5 minutes of time. Preferably from 30 seconds to 4 minutes. Preferably from 1 minute to 4 minutes. In this case, a brush can be additionally used.

Thus, the composition proposed in the scope of the present invention can be used in healthcare, providing effective prevention and/or treatment of the oral diseases.

The invention claimed is:

1. A composition for the treatment and/or prevention of the oral diseases comprising an effective amount of aqueous and lipophilic $CO_2$ extracts of aspen bark and at least one or more auxiliary substances for the treatment and/or prevention, wherein the quantitative ratio of aqueous and lipophilic $CO_2$ extracts of aspen bark is 1:0.3-30:1 by weight.

2. The composition according to claim 1, wherein one or more of the following substances are used as an auxiliary substance: a thickener, a binding agent, an abrasive agent, a wetting agent, a foaming agent, a flavor, a sweetener, a stabilizer, a preservative.

3. The composition according to claim 1 or 2, further comprising anti-carious additives.

4. The composition according to claim 1, wherein the quantitative ratio of aqueous and $CO_2$ lipophilic extracts of aspen bark is 1:1, 2:1, 5:1, 10:1, or 20:1 by weight.

5. The composition according to claim 1, wherein the therapeutic and/or preventive action is aimed at acute and chronic forms of stomatitis, periodontal diseases, which are gingivitis, periodontitis or parodontosis, dental caries or pulpitis.

6. The composition according to claim 1, wherein treatment and/or prevention of the oral diseases caused by burning hot food, injuring the oral cavity with a sharp object, or chemical burn.

7. The composition according to claim 1, wherein the components are the following:

| Component | %, wt. |
|---|---|
| Sorbitol | 40 |
| Xylitol | 8 |
| Silicon dioxide (abrasive) | 5 |
| Sodium Fluoride | 0.3 |
| Xanthan gum | 0.8 |
| Water extract of aspen bark | 2 |
| $CO_2$ extract of aspen bark | 0.2 |
| Alkylamidobetaine | 0.6 |
| Sodium lauroylsarcosinate | 0.5 |
| Sodium Benzoate | 0.8 |
| Potassium Sorbate | 0.2 |
| Sodium saccharin | 0.05 |
| O-cumene-5-ol | 0.05 |
| Flavoring agent | 0.6 |
| Water | Up to 100. |

8. The composition according to claim 1, wherein the components are the following:

| Component | % wt. |
|---|---|
| Sorbitol | 20 |
| Xylitol | 15 |
| Silicon dioxide (abrasive) | 15 |
| Sodium Fluoride | 0.1 |
| Xanthan gum | 1.2 |
| Water extract of aspen bark | 3 |
| $CO_2$ extract of aspen bark | 0.1 |
| Alkylamidobetaine | 0.8 |
| Sodium lauroylsarcosinate | 0.2 |
| Sodium Benzoate | 0.5 |
| Potassium Sorbate | 0.4 |
| Sodium saccharin | 0.2 |
| O-cumene-5-ol | 0.08 |
| Flavoring agent | 1.2 |
| Water | Up to 100. |

9. The composition according to claim 1, wherein the aqueous extract of aspen bark comprises no more than 95% by weight of water and volatile substances.

10. The composition according to claim 1, wherein the $CO_2$ lipophilic extract of aspen bark comprises no more than 60% by weight of water and volatile substances.

11. The composition according to claim 1, wherein the product is a toothpaste, mouthwash or non-abrasive gel applied to the surface of the teeth.

12. The composition according to claim 1 to be applied to the surface of the teeth for the treatment and/or prevention of the oral diseases.

13. A method for the treatment and/or prevention of the oral diseases, which comprises applying a composition according to claim 1 to the surface of the teeth and finding the composition in the oral cavity for 5 seconds to 5 minutes of time.

14. The method according to claim 13, wherein the residence time of the composition is from 30 seconds to 5 minutes.

* * * * *